United States Patent
Hwang et al.

(10) Patent No.: US 9,854,968 B2
(45) Date of Patent: Jan. 2, 2018

(54) BEHIND-EYE MONITORING USING NATURAL REFLECTION OF LENSES

(71) Applicant: International Business Machines Corporation, Armonk, NY (US)

(72) Inventors: Inseok Hwang, Austin, TX (US); Su Liu, Austin, TX (US); Eric J. Rozner, Austin, TX (US); Chin Ngai Sze, Austin, TX (US); Chungkuk Yoo, Daejeon (KR)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/159,913

(22) Filed: May 20, 2016

(65) Prior Publication Data

US 2017/0332901 A1  Nov. 23, 2017

(51) Int. Cl.
A61B 3/14 (2006.01)
A61B 3/00 (2006.01)
A61B 3/113 (2006.01)

(52) U.S. Cl.
CPC ............ *A61B 3/113* (2013.01); *A61B 3/14* (2013.01)

(58) Field of Classification Search
USPC ................................................. 351/200–246
See application file for complete search history.

(56) References Cited

U.S. PATENT DOCUMENTS

| | | | |
|---|---|---|---|
| 5,233,465 A | 8/1993 | Wheatley et al. | |
| 8,165,347 B2 | 4/2012 | Heinzmann et al. | |
| 8,488,243 B2 * | 7/2013 | McKnight | A63F 13/06 359/237 |
| 8,878,749 B1 * | 11/2014 | Wu | G01S 17/06 345/8 |
| 9,107,622 B2 * | 8/2015 | Nistico | A61B 3/0008 |
| 2010/0220291 A1 * | 9/2010 | Horning | G02B 27/017 351/210 |
| 2013/0066213 A1 * | 3/2013 | Wellington | A61B 3/112 600/475 |

FOREIGN PATENT DOCUMENTS

| | | |
|---|---|---|
| CN | 204009234 U | 12/2014 |
| CN | 105159450 A | 12/2015 |

(Continued)

OTHER PUBLICATIONS

Cortes Torres et al.; "Workload Assessment with eye Movement Monitoring Aided by Non-invasive and Unobtrusive Micro-fabricated Optical Sensors"; UIST '15 Adjunct, Nov. 8-11, 2015; pp. 53-54; ACM.

(Continued)

*Primary Examiner* — Mohammed Hasan
(74) *Attorney, Agent, or Firm* — Alexa L. Ashworth; Brian M. Restauro

(57) ABSTRACT

A system and method for eye monitoring using the natural reflections of the lenses and human eyes. The system includes a frame worn on the head of a user containing side supports and lenses. A light source and a camera are mounted on the side supports, so that they are located behind the eyes of the user, when the system is being worn by the user. The camera captures the natural light reflections from the lenses and the eye retinas, and uses the data to calculate a position or orientation of a user gaze.

19 Claims, 2 Drawing Sheets

(56) References Cited

FOREIGN PATENT DOCUMENTS

GB      2480193 B      1/2015
HK      1146843 A1      5/2014

OTHER PUBLICATIONS

Morimoto et al.; "Frame-Rate Pupil Detector and Gaze Tracker"; Proceedings of IEEE ICCV; 1999; 5 pages.
Morimoto et al.; "Pupil Detection and Tracking Using Multiple Light Sources"; Image and Vision Computing, 18; 2000; pp. 331-335.
Wong; "Eye "R" Glasses: Development of an Infrared Sensor System for Detecting the Human Body"; A Thesis presented to the Faculty of California Polytechnic State University, San Luis Obispo; Jun. 2013; pp. 1-96.
"SMI Eye Tracking Glasses 2 Wireless"; © Copyright 2016 SensoMotoric Instruments GmbH; smi_flyer_ETG_120Hz; Mar. 2, 2016; 4 pages; <www.eyetracking-glasses.com>.
"Tobii Pro Glasses 2: Product Description"; Version 1.0.8; Nov. 2015; Copyright © Tobii AB (publ); pp. 1-17.

\* cited by examiner

BEHIND-EYE MONITORING USING NATURAL REFLECTION OF LENSES

BACKGROUND OF THE INVENTION

The present invention relates generally to the field of eye tracking, and more particularly to monitoring a user's gaze using behind-eye monitoring and the natural reflection of lenses.

Eye tracking is the measurement of eye activity, including where a user is looking, when a user blinks, and a user's reaction to various stimuli. Data from eye tracking may be collected using a head-mounted eye tracker, connected to a computing device. Generally, eye trackers include at least a light source and a camera, which are used to track data involving the reflection of light. This data is then ultimately used to determine the direction of a user's gaze. Eye tracking may allow for the discovery of hidden data, such as a user's point of interest, demand, and mental status, in a highly precise and real-time manner. Presently, the use of eye tracking glasses is mostly limited to the experimental labs and usage by selective participants.

SUMMARY

According to an embodiment of the present invention, a system for eye monitoring is provided. The system comprises: a frame configured to be worn on a head of a user, the frame coupled to a first side support and a second side support, the first and second side supports each configured to rest on an ear of the user; at least one lens coupled to the frame; a first light source coupled to the first side support, wherein the first light source is located behind an eye of the user; and a first camera coupled to the first side support, wherein the first camera is located behind the eye of the user, and wherein the first camera is configured to receive light that is reflected from the at least one lens.

According to another embodiment of the present invention, a method for eye monitoring is provided. The method comprises: from a first light source located behind an eye of a user, emitting an infrared light source toward at least one lens, wherein the infrared light source is reflected off of the at least one lens; and capturing, by a first camera located behind the eye of the user, a retro reflected light, wherein the retro reflected light is configured to reflect off of the at least one lens prior to being captured by the first camera.

According to another embodiment of the present invention, a computer program product for eye monitoring is provided. The computer program product comprises: from a first light source located behind an eye of a user, program instructions to emit an infrared light source toward at least one lens, wherein the infrared light source is reflected off of the at least one lens; and program instructions to capture, by a first camera located behind the eye of the user, a retro reflected light, wherein the retro reflected light is configured to reflect off of the at least one lens prior to being captured by the first camera.

DETAILED DESCRIPTION

Eye tracking sensors can be embedded into various glasses, and record eye orientation (i.e., the direction of the eye gaze). Embodiments of the present invention recognize that eye tracking and monitoring is a strong indicator of a user's point of interest and can be a source of data for predictive analytics of a user's behavior (e.g., purchase information or healthcare). Embodiments of the present invention recognize that placing the sensors and circuitry involved in eye monitoring behind the eyes of a user minimizes obstructions in the user's field of view and places less of a weight burden on the user's front face and nose (i.e., higher degree of user comfort than circuitry placed on the front of an eye tracking device). Embodiments of the present invention recognize that placing the sensors and circuitry behind the eyes of a user is more socially friendly and makes for an everyday wearable device, instead of a special purpose use or experimental use. Embodiments of the present invention provide systems and methods for monitoring eye movement by placing a camera and light source behind the eyes of a user, and using the natural reflection properties of eyes to capture and track the reflected light.

Figure 1A:
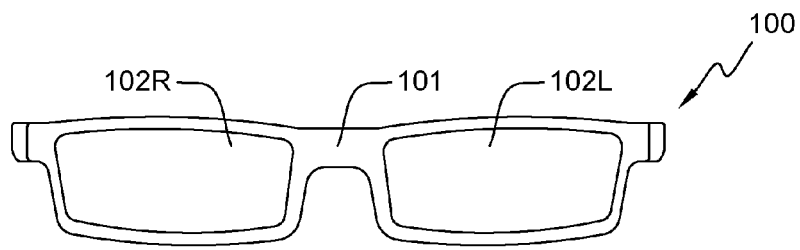
FIG. 1A depicts a front view of an eye monitoring device, in accordance with an embodiment of the present invention.
Figure 1B:
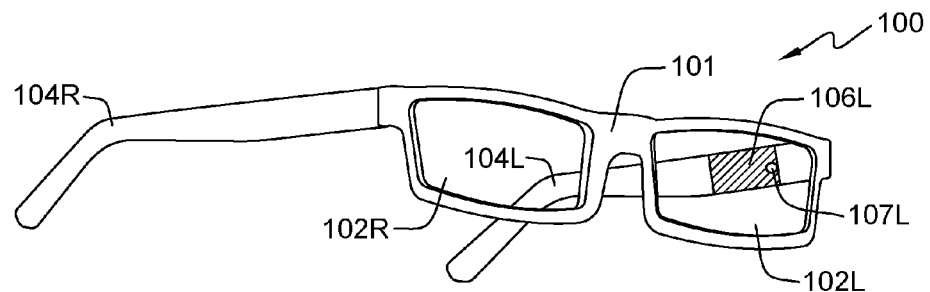
FIG. 1B depicts a perspective view of the eye monitoring device of FIG. 1A, in accordance with an embodiment of the present invention.
Figure 1C:
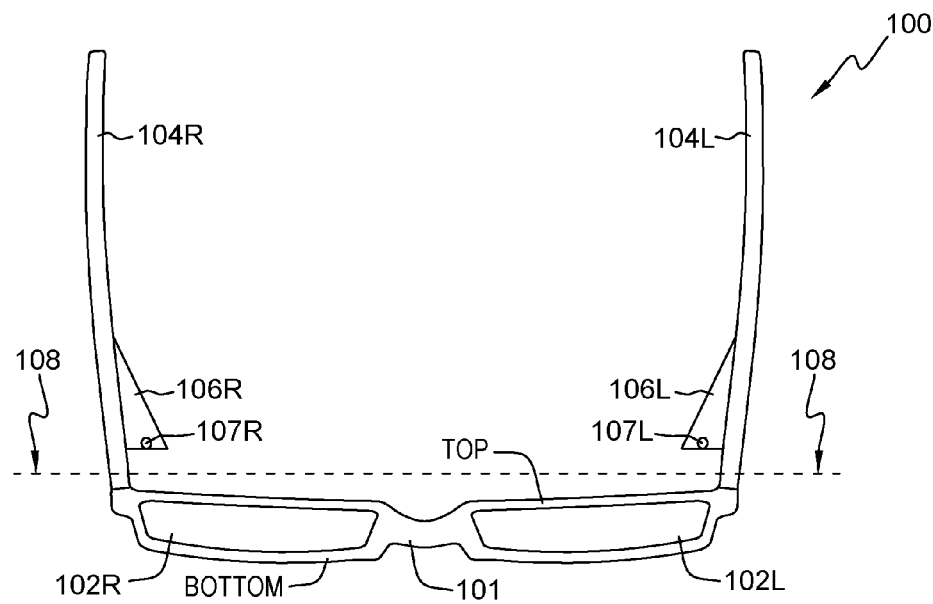
FIG. 1C depicts a top view of the eye monitoring device of FIG. 1A, in accordance with an embodiment of the present invention.

The present invention will now be described in detail with reference to the Figures. FIGS. 1A to 1C depict an eye monitoring device 100, in accordance with an embodiment of the present invention. Modifications to eye monitoring device 100 may be made by those skilled in the art without departing from the scope of the invention as recited by the claims.

In this exemplary embodiment, eye monitoring device 100 may be integrated into a pair of eye glasses, designed such that a user can wear them on their head like a normal pair of glasses. Eye monitoring device 100 can be, for example, smart glasses, prescription glasses, sunglasses, or any other type of wearable devices known in the art. In this exemplary embodiment, eye monitoring device 100 includes frame 101 with two side supports 104L and 104R, which are configured to support eye monitoring device 100 and rest on the ears of the user who is wearing the device. As depicted in FIGS. 1B and 1C, side supports 104L and 104R are hinged to the front part of frame 101. Frame 101 may be configured like any one of numerous glasses frames that may be worn by a user, known in the art (e.g., thicker frame, thinner frame, or composed of various materials).

In this exemplary embodiment, frame 101 contains two openings for lenses 102L and 102R. Lenses 102L and 102R are each coupled to frame 101, and configured to be adjacent to the eyes of a user, when eye monitoring device 100 is worn by the user. The distance between the eyes of the user and lenses 102L and 102R is that of the typical eye-to-lens distance of glasses known in the art, for example between 1 and 2 centimeters. In other embodiments, frame 101 may be configured such that lenses 102L and 102R are integrally formed as one lens. In this exemplary embodiment, lenses 102L and 102R are partially or completely coated with an infrared reflecting visibly transparent film known in the art, wherein the film is configured to reflect wavelengths of light in the infrared region of the spectrum, while being substantially transparent to wavelengths of light in the visible spectrum. A color masking film may be associated with the infrared reflecting film.

Cameras 106L and 106R and light sources 107L and 107R are mounted on each of side supports 104L and 104R, respectively. Light sources 107L and 107R are infrared light sources, and cameras 106L and 106R are infrared cameras, configured to capture the infrared light. In this exemplary embodiment, cameras 106L and 106R are coupled to, and controlled by, processing circuitry (not pictured) to follow the movement of the user's eyes. The processing circuitry may be configured to control light emission from at least one of infrared light sources 107L and 107R and to receive data associated with the reflected light from cameras 106L and 106R. Cameras 106L and 106R each contain sensors (not pictured). Cameras 106L and 106R are configured to capture reflected infrared light, and operate in conjunction with the sensors and processing circuitry to track and record eye movement (i.e., eye orientation, direction of gaze, etc.). Each of cameras 106L and 106R (including the sensors and processing circuitry) and infrared light sources 107L and 107R, are positioned behind eye line 108, such that cameras 106L and 106R (and accompanying infrared light sources 107L and 107R) are located behind the eyes of a user when the user is wearing eye monitoring device 100, as depicted in FIG. 1C.

Figure 2:
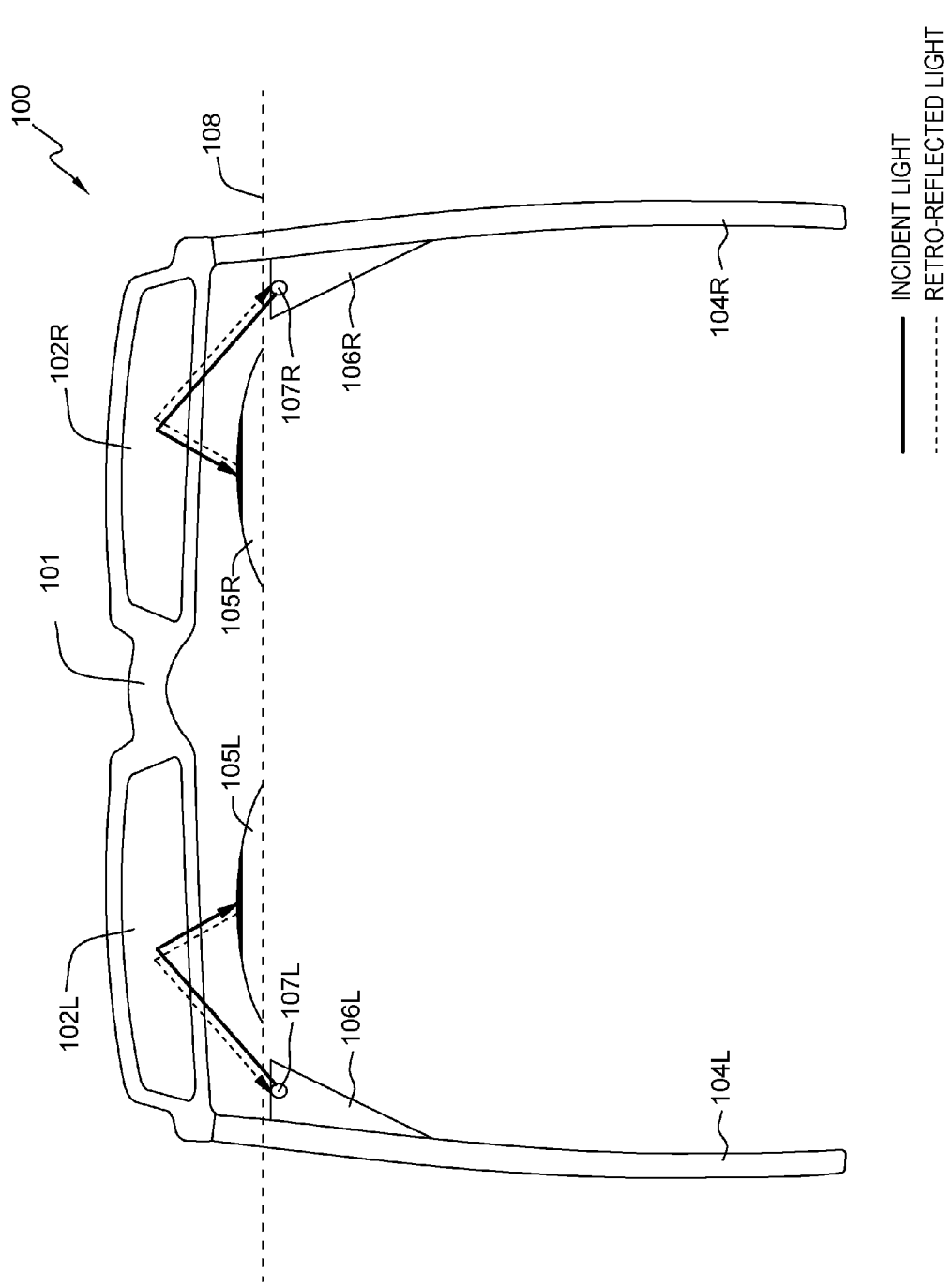
FIG. 2 depicts a top view of the eye monitoring device of FIG. 1A, illustrating incident and retro reflected light, in accordance with an embodiment of the present invention.

FIG. 2 depicts a top view of the eye monitoring device of FIG. 1A, illustrating incident and retro reflected light, in accordance with an embodiment of the present invention.

As depicted in FIG. 2, eyes 105L and 105R are positioned in front of eye line 108, which runs parallel to the front-most surface of cameras 106L and 106R. Thus, cameras 106L and 106R are situated behind eyes 105L and 105R, respectively. In this exemplary embodiment, incident light is emitted from infrared light sources 107L and 107R toward lenses 102L and 102R, respectively. The incident light is reflected off the lenses 102L and 102R toward each of eyes 105L and 105R. Retro reflected light from the retinas of eyes 105L and 105R is then reflected back toward lenses 102L and 102R. Retro reflected light is a natural property of human eye corneas in which light is reflected with a minimum of scattering, and at a vector path that is parallel to, but opposite direction from, the light source. The retro reflected light then reflects off lenses 102L and 102R (at the same angle of the light source, but in the opposite direction) and is captured by cameras 106L and 106R, respectively.

In some embodiments, the direction of a user's gaze can be determined based on the natural light reflecting properties of the human eyes, whereby light reflects off of the front surface (i.e., the cornea) of a user's eyes 105L and 105R. In this exemplary embodiment, the direction of a user's gaze is determined using light reflections off of both the cornea of the user's eyes 105L and 105R, and the retina of the user's eyes 105L and 105R. The differences in location of the retro reflected infrared light captured by cameras 106L and 106R are used to determine the gaze orientation and direction of the user. These differences are created by the shape of the cornea of the eye, which causes the incident light to reflect off of the eye at different angles, depending on the direction a user is gazing relative to the infrared light source(s) 107L and 107R. The difference in angle of the captured, reflected light may then be used to determine a gaze direction of the user.

When infrared light sources (i.e., incident light) 107L and 107R are projected into eyes 105L and 105R, several natural light reflections occur on the boundaries of the lens and cornea (i.e., the Purkinje images). Purkinje images are known in the art, and are reflections of objects from the structure of the eye. At least four Purkinje images are usually visible, where the first image is the reflection from the outer surface of the cornea (i.e., corneal reflection or glint) and the fourth image is the reflection from the inner surface of the lens. In some embodiments, the first and fourth Purkinje images are used by eye monitoring device 100 to measure the position of the eye. The first Purkinje image, along with the reflection of the infrared light off of the retina (i.e., the 'bright eye' effect), can be video recorded using IR sensitive cameras 106L and 106R, as a very bright spot and a less bright disc, respectively. When the eyes 105L and 105R move horizontally or vertically, the relative positioning of the glint and the center of the bright eye change accordingly, and the direction of the user's gaze from a relative position can be calculated, using known techniques in the art, which can be known computations and algorithms, as well as complex calculations and algorithms to account for changes in movement and focus of the eyes and their images.

In this exemplary embodiment, the infrared light source(s) (i.e., the incident light) is directed toward lenses 102L and 102R, in contrast to existing eye tracking devices where the infrared light source is located in front of the eyes, and the incident light is often directed toward the user's eyes. The infrared light source(s) are then reflected off of lenses 102L and 102R toward the user's eyes 105L and 105R.

In this embodiment, eye monitoring device 100 detects and tracks the pupil of eyes 105L and 105R, and estimates the point of gaze, which also requires the detection of the corneal reflections (i.e., the 'glint' or the bright spot close to the pupils) created by infrared light sources 107L and 107R. The glint (the corneal reflection) of the eyes 105L and 105R can be tracked using the geometrical and physiological properties of the human eye. Corneal reflections are known in the art, and can be detected under various illumination conditions. For example, bright and dark pupil images can be obtained, and the corneal reflections from the on/off light sources can be easily identified as the bright regions in the iris of the eyes. Pupils can be detected from a threshold of the difference of the dark pupil images, from the bright pupil images.

In this exemplary embodiment, due to the natural retro reflectivity property of eyes 105L and 105R, a bright pupil image is seen by cameras 106L and 106R when a light source 107L and 107R is placed very close to its optical axis (this is also known as the "red-eye effect"). When the light source is not on the camera's optical axis, a dark pupil is seen. Pupil detection combines the dark and bright pupil images, where pupil candidates are detected from the threshold difference of the dark from the bright pupil image. In this exemplary embodiment, the retro reflective property of the eyes can be leveraged by placing the infrared light source 107L and 107R close to the optical axis of cameras 106L and 106R. As the incident infrared light reflects off of the retina of eyes 105L and 105R, the light is retro reflected back to lenses 102L and 102R, which then retro reflects the light back to cameras 106L and 106R, where the light is captured and processed for gaze tracking. In some embodiments, the pupils can be detected from the threshold difference of the bright and dark pupil images obtained. After a known calibration procedure, the vector computed from the pupil center to the center of the corneal glints generated from the light sources can then be used to estimate the gaze position and point of gaze.

In this exemplary embodiment, cameras 106L and 106R track the reflection of the infrared light source(s) 107L and 107R along with visible ocular features, such as the pupil of eyes 105L and 105R. This data is used to extrapolate the rotation and orientation of eyes 105L and 105R, and ultimately the direction of the user's gaze. Additional information such as frequency of blinking and changes in pupil size may also be detected.

Eye gaze tracking and monitoring estimates the position on a screen or point of interest to where the user is fixating their gaze. In this exemplary embodiment, the user's pupil and the corneal reflection are tracked, and the coordinates of the pupil tracker are mapped to the screen or the fixed point coordinates. The surface of eyes 105L and 105R can be approximated to a sphere and, as the light sources 107L and 107R are fixed, the glint on the cornea of eyes 105L and 105R can be taken as a reference point, thus the vector from the glint to the center of the pupil can describe the gaze direction. To estimate the screen coordinates where the user is looking, a second order polynomial transformation can be used.

Eye gaze tracking is often a strong indicator of a user's point of interest, mental processes, or an internal emotion. Thus, eye gaze tracking systems may be used as a cognitive input modality and can be a source of data for predictive analytics, such as a user's behaviors or demands (e.g., purchases, seeking information, emotional or mental healthcare). Accordingly, by placing the camera and circuitry behind a user's eyes on the eye monitoring device 100 described in FIGS. 1A-C and FIG. 2, eye tracking devices may become more common in everyday use by having the ability to be integrated with normal eyewear and without obstructing the user's view during the course of normal wear.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A system for eye monitoring, comprising:
   a frame configured to be worn on a head of a user, the frame coupled to a first side support and a second side support, the first and second side supports each configured to rest on an ear of the user;
   at least one lens coupled to the frame;
   a first light source coupled to the first side support, wherein the first light source is located behind an eye of the user;
   a first camera coupled to the first side support, wherein the first camera is located behind the eye of the user, and wherein the first camera is configured to receive light that is reflected from the at least one lens;
   a second light source coupled to the second side support, wherein the second light source is located behind another eye of the user; and
   a second camera coupled to the second side support, wherein the second camera is located behind the other eye of the user, and wherein the second camera is configured to receive another light that is reflected from the at least one lens.

2. The system of claim 1, wherein the first light source is configured to emit an infrared light.

3. The system of claim 2, wherein the first light source is configured to emit the infrared light toward the at least one lens coupled to the frame.

4. The system of claim 1, wherein the first light source is operatively coupled to the first camera.

5. The system of claim 1, wherein an incident light from the first light source is configured to reflect off of the at least one lens prior to reflecting off of a retina of the eye of the user.

6. The system of claim 5, wherein a light reflected off of the retina of the eye of the user is retro reflected light configured to follow a same path in an opposite direction as the incident light, and wherein the first camera is configured to capture the retro reflected light.

7. The system of claim 6, wherein the incident light is configured to reflect off of the retina of the eye of the user at a same angle as the retro reflected light is reflected off of the eye of the user.

8. The system of claim 6, wherein the incident light is configured to reflect off of the at least one lens at a same angle as the retro reflected light is configured to reflect off of the at least one lens.

9. The system of claim 6, wherein the incident light and the retro reflected light are used to record a plurality of images.

10. The system of claim 6, wherein data associated with the captured retro reflected light from the first camera is used to calculate a user gaze position.

11. The system of claim 1, wherein the at least one lens is coated with an infrared reflecting visibly transparent film.

12. The system of claim 1, further comprising:
    processing circuitry, wherein the processing circuitry is configured to control an emission of light from the first light source, and wherein the processing circuitry is configured to receive data associated with retro reflected light from the first camera.

13. The system of claim 1, wherein the first camera and the second camera are infrared sensitive cameras.

14. A method for eye monitoring, comprising:
    from a first light source located behind an eye of a user, emitting an infrared light source toward at least one lens, wherein the infrared light source is reflected off of the at least one lens;
    from a second light source located behind another eye of the user, emitting another infrared light source toward the other eye;
    capturing, by a first camera located behind the eye of the user, a retro reflected light, wherein the retro reflected light is configured to reflect off of the at least one lens prior to being captured by the first camera; and
    capturing, by a second camera located behind the eye of the user another retro reflected light from the at least one lens.

15. The method of claim 14, wherein the emitted infrared light source and the retro reflected light follow a same path in opposite directions and reflect off of the at least one lens at a same angle.

16. The method of claim 14, further comprising:
    calculating, from data associated with the captured retro reflected light, a user gaze position.

17. The method of claim 16, further comprising:
    wherein the calculated user gaze position is input as a source of data for predictive analytics.

18. A computer program product for eye monitoring, comprising:
    from a first light source located behind an eye of a user, program instructions to emit an infrared light source toward at least one lens, wherein the infrared light source is reflected off of the at least one lens;
    from a second light source located behind another eye of the user, emitting another infrared light source toward the other eye;

program instructions to capture, by a first camera located behind the eye of the user, a retro reflected light, wherein the retro reflected light is configured to reflect off of the at least one lens prior to being captured by the first camera; and capturing, by a second camera located behind the eye of the user another retro reflected light from the at least one lens.

19. The computer program product of claim 18, wherein the emitted infrared light source and the retro reflected light follow a same path in opposite directions and reflect off of the at least one lens at a same angle.

\* \* \* \* \*